United States Patent
Ken et al.

[11] Patent Number: 6,033,423
[45] Date of Patent: *Mar. 7, 2000

[54] MULTIPLE LAYERED VASO-OCCLUSIVE COILS

[75] Inventors: Christopher G. M. Ken, San Mateo; Erik T. Engelson, Menlo Park, both of Calif.

[73] Assignee: Target Therapeutics, Inc., Fremont, Calif.

[*] Notice: This patent is subject to a terminal disclaimer.

[21] Appl. No.: 08/974,275

[22] Filed: Nov. 19, 1997

Related U.S. Application Data

[63] Continuation of application No. 08/779,378, Jan. 7, 1997, Pat. No. 5,749,891, which is a continuation of application No. 08/466,039, Jun. 6, 1995, abandoned.

[51] Int. Cl.$^7$ .................................................. A61B 17/00
[52] U.S. Cl. .............................. 606/200; 606/191; 623/1
[58] Field of Search ....................... 623/1, 12; 606/191, 606/108, 200, 198, 151

[56] References Cited

U.S. PATENT DOCUMENTS

| | | |
|---|---|---|
| 2,869,858 | 1/1959 | Hartwell . |
| 3,174,851 | 3/1965 | Buehler et al. . |
| 3,351,463 | 11/1967 | Rozner et al. . |
| 3,753,700 | 8/1973 | Harrison et al. . |
| 4,994,069 | 2/1991 | Ritchart et al. . |
| 5,108,407 | 4/1992 | Geremia et al. . |
| 5,122,136 | 6/1992 | Guglielmi et al. . |
| 5,147,400 | 9/1992 | Kaplan et al. . |
| 5,226,911 | 7/1993 | Chee et al. . |
| 5,234,437 | 8/1993 | Sepetka . |
| 5,250,071 | 10/1993 | Palermo . |
| 5,261,916 | 11/1993 | Engelson . |
| 5,280,888 | 1/1994 | Brandener . |
| 5,304,194 | 4/1994 | Chee et al. . |
| 5,304,195 | 4/1994 | Twyford, Jr. et al. . |
| 5,312,415 | 5/1994 | Palermo . |
| 5,350,397 | 9/1994 | Palermo et al. . |
| 5,354,295 | 10/1994 | Guglielmi et al. . |
| 5,382,259 | 1/1995 | Phelps et al. . |
| 5,476,472 | 12/1995 | Dormandy, Jr. et al. . |
| 5,522,836 | 6/1996 | Palermo . |
| 5,639,277 | 6/1997 | Mariant et al. .......................... 606/191 |
| 5,749,891 | 5/1998 | Ken et al. ................................. 606/200 |

FOREIGN PATENT DOCUMENTS

3203410  11/1982  Germany .

*Primary Examiner*—Bruce E. Snow
*Attorney, Agent, or Firm*—Morrison & Foerster, LLP

[57] ABSTRACT

This is an implantable vaso-occlusive device. It is a complex, helically wound coil having multiple secondary layers of primary windings. The final shape is often chunky in nature and may be used in the approximate shape of an anatomical cavity. It may be deployed in the approximate shape of a sphere, an ovoid, or other distorted spherical shape. The device is a self-forming shape made from a pre-formed linear vaso-occlusion member. Fibers may be introduced onto the device and affixed to the pre-formed linear member. The constituent member may be also be covered with a fibrous braid. The device is typically introduced through a catheter. The device is passed axially through the catheter sheath and assumes its form upon exiting the catheter without further action. The invention also includes methods of winding the anatomically shaped vaso-occlusive device into appropriately shaped forms and annealing them to form various devices.

26 Claims, 9 Drawing Sheets

MULTIPLE LAYERED VASO-OCCLUSIVE COILS

This application is a continuation of application Ser. No. 08/779,378, filed Jan. 7, 1997, now U.S. Pat. No. 5,749,891, which is a continuation of application of Ser. No. 08/466,039, filed Jun. 6, 1995, now abandoned.

FIELD OF THE INVENTION

This invention is an implantable vaso-occlusive device. It is a complex, helically wound coil having multiple secondary layers of primary windings. The final shape is often chunky in nature and may be used in the approximate shape of an anatomical cavity and tends to be more space-filling than single layered vaso-occlusive coils. It may be deployed in the approximate shape of a sphere, an ovoid, or other distorted spherical shape. The device is a self-forming shape made from a pre-formed linear vaso-occlusion member. Fibers may be introduced onto the device and affixed to the pre-formed linear member. The constituent member may be also be covered with a fibrous braid. The device is typically introduced through a catheter. The device is passed axially through the catheter sheath and assumes its form upon exiting the catheter without further action. The invention also includes methods of winding the anatomically shaped vaso-occlusive device into appropriately shaped forms and annealing them to form various devices.

BACKGROUND OF THE INVENTION

Vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vaso-occlusive device is a helical wire coil having windings which may be dimensioned to engage the walls of the vessels. Other less stiff helically coiled devices have been described, as well as those involving woven braids.

For instance, U.S. Pat. No. 4,994,069, to Ritchart et al., describes a vaso-occlusive coil that assumes a linear helical configuration when stretched and a folded, convoluted configuration when relaxed. The stretched condition is used in placing the coil at the desired site (by its passage through the catheter) and the coil assumes a relaxed configuration—which is better suited to occlude the vessel—once the device is so placed. Ritchart et al. describes a variety of shapes. The secondary shapes of the disclosed coils include "flower" shapes and double vortices. A random shape is described, as well.

Vaso-occlusive coils having attached fibrous elements in a variety of secondary shapes are shown in U.S. Pat. No. 5,304,194, to Chee et al. Chee et al. describes a helically wound device having a secondary shape in which the fibrous elements extend in a sinusoidal fashion down the length of the coil. These coils, as with Ritchart et al., are produced in such a way that they will pass through the lumen of a catheter in a generally straight configuration and, when released from the catheter, form a relaxed or folded shape in the lumen or cavity chosen within the human body. The fibrous elements shown in Chee et al. enhance the ability of the coil to fill space within the vasculature and to facilitate formation of embolus and subsequent allied tissue.

There are a variety of ways of discharging shaped coils and linear coils into the human vasculature. In addition to those patents which apparently describe only the physical pushing of a coil out into the vasculature (e.g., Ritchart et al.), there are a number of other ways to release the coil at a specifically chosen time and site. U.S. Pat. No. 5,354,295 and its parent, U.S. Pat. No. 5,122,136, both to Guglielmi et al., describe an electrolytically detachable embolic device.

A variety of mechanically detachable devices are also known. For instance, U.S. Pat. No. 5,234,437, to Sepetka, shows a method of unscrewing a helically wound coil from a pusher having interlocking surfaces. U.S. Pat. No. 5,250,071, to Palermo, shows an embolic coil assembly using interlocking clasps mounted both on the pusher and on the embolic coil. U.S. Pat. No. 5,261,916, to Engelson, shows a detachable pusher-vaso-occlusive coil assembly having an interlocking ball and keyway-type coupling. U.S. Pat. No. 5,304,195, to Twyford et al., shows a pusher-vaso-occlusive coil assembly having an affixed, proximately extending wire carrying a ball on its proximal end and a pusher having a similar end. The two ends are interlocked and disengage when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and will then be released upon pushing the axially placed pusher wire against the member found on the proximal end of the vaso-occlusive coil.

Vaso-occlusive coils having little or no inherent secondary shape have also been described. For instance, in U.S. patent application Ser. No. 07/978,320, filed Nov. 18, 1992, entitled "Ultrasoft Embolization Coils with Fluid-Like Properties" by Berenstein et al., is found a coil having little or no shape after introduction into the vascular space.

None of these devices are multiple winding helical coils which self-form into layered complex helical shapes upon ejection from a delivery catheter.

SUMMARY OF THE INVENTION

This invention is a vaso-occlusive device comprising one or more vaso-occlusive helical coils which are formed by first winding a wire into a first helix; the first helix is then wound into a secondary form which is wound back onto itself to form two or more layers of the primary coil. The reverse winding may be on the same axis as the first winding axis or may be on a different axis. The overall form may be selected to be a generally spherical or ovoid shape when relaxed. Desirably, the vaso-occlusive device is of a size and shape suitable for fitting snugly within a vascular cavity (e.g., an aneurysm, or perhaps, a fistula). The stiffness of the various parts of the coil may be selected to enhance the utility of the device for specific applications. Fibrous materials may be woven into the member or tied or wrapped onto it.

The device may be made in a variety of ways. Typically, the member is helically wound in a generally linear fashion to form a first or primary winding. After completion of that step, the primary winding is then wound around a first appropriately shaped mandrel or form, a cylindrical mandrel or form may then be placed over the first layer. The primary coil is then wound back over the first layer of coil and cylindrical mandrel until a suitable length is attained. A further cylindrical mandrel may then be placed over the second layer of layered coil and a further layer of primary coil is then wound back across the second cylindrical mandrel. Further mandrels and reverses in direction may be had as desired. The assembly may then be heat-treated to help it retain its shape after removal from the heating form. Auxiliary fibrous materials are then added by weaving, tying, or other suitable permanent attachment methods.

The device is used simply by temporarily straightening the device and introducing it into a suitable catheter, the catheter already having been situated so that its distal opening is within the mouth of the vascular cavity or opening to be filled. The device is then pushed through the catheter and, upon its ejection from the distal end of the catheter into the vascular cavity, assumes its relaxed shape.

The device is typically used in the human vasculature to form emboli but may be used in any site in the human body where an occlusion such as one produced by the inventive device is needed.

DESCRIPTION OF THE INVENTION

Figure 1A:
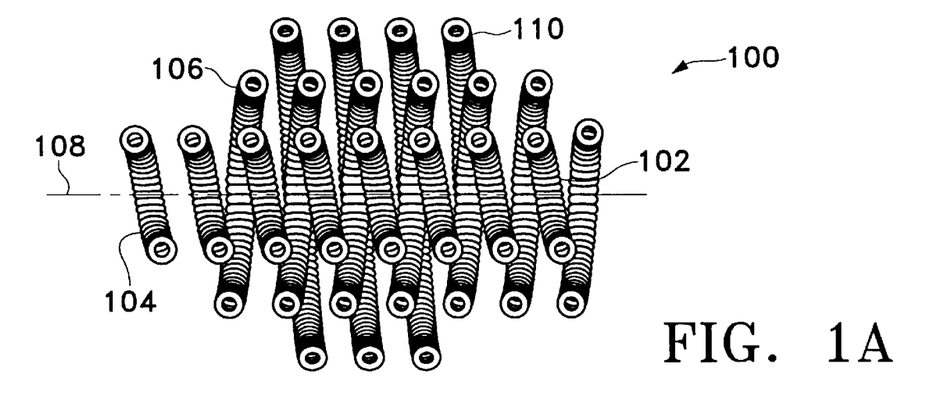
FIG. 1A shows a cross sectional side view of a vaso-occlusive coil made according to the invention.

FIG. 1A shows a side-view cross-section of one highly desirable variation of this invention—a generally spherical coil (100). The variation shown in FIG. 1A (and the others shown in the Figures) is a "coil of a coil". That is to say that the overall device (100) is made up of a primary coil (102) which has been initially wound in a linear form and then wound into the secondary form shown. This coil (100) has three layers of secondary windings. The inner winding (104) first wound and the second layer (106) is found on top of the first layer (104). The second layer (106) in this instance has approximately the same longitudinal axis (108). The second layer (106) is formed simply by winding the primary coil (102) in the opposite direction from that of the first layer (104). The procedure for winding the coil will be described in greater below. Although it is not absolutely necessary for the invention, the second layer (106) may be a continuation of the primary coil (102) of the first layer (104). In some circumstances, it may be desirable to use multiple primary coils. In the FIG. 1B variation, the vaso-occlusive coil is made up of an outer layer (110). As may be seen in both FIGS. 1A and 1B, the outer layer (110) is shorter in axial length than the second layer (106) which, in turn, is shorter than the axial length than the inner layer (104). This configuration is a chunky or stepped shape approximating a sphere, ovoid, or egg. Other shapes approximating the shape of the interior of a vascular cavity (e.g., an aneurysm, or perhaps, a fistula) are contemplated and may be easily formulated using the concepts described herein.

Figure 1B:
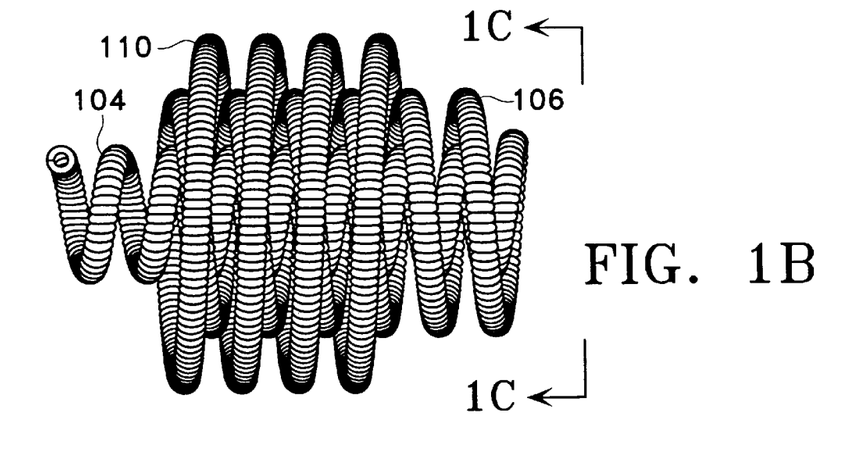
FIG. 1B shows a side view of the vaso-occlusive coil of FIG. 1A.
Figure 1C:
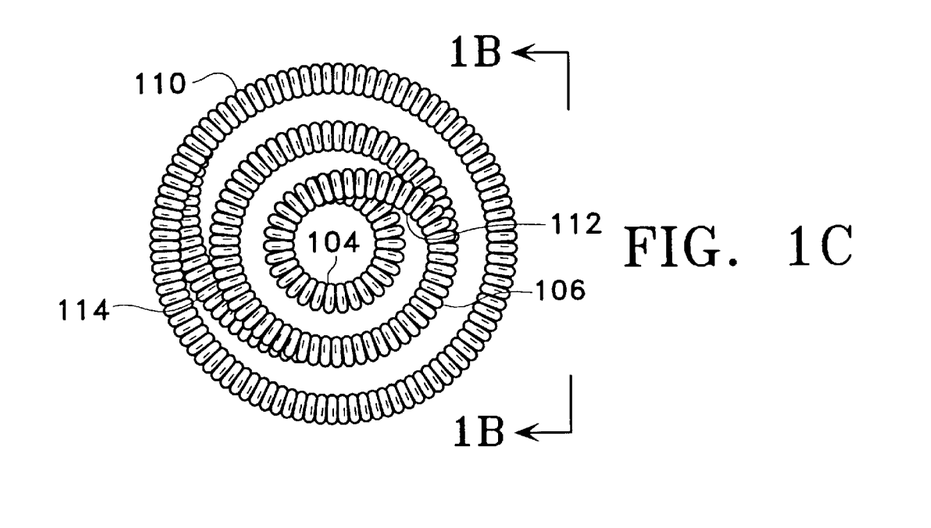
FIG. 1C shows a end view of the vaso-occlusive coil of FIG. 1A.

FIG. 1C shows an end view of the device (100) shown in FIGS. 1A and 1B. FIG. 1C shows the inner layer (104), second layer (106), and outer layer (110). Connecting inner layer (104) and second layer (106) may be seen the connecting coil section (112). Similarly, connecting coil section (114) is seen between second layer (106) and outer layer (110).

The spacing between the various layers is not critical but is desirably somewhat loose, much in the way depicted in the Figures. This spacing places a significant amount of thrombogenic material within the inner recesses of the inventive device. Furthermore, the spacing allows room for the expansion of the device and self-alignment into the desired shape as the primary coil extends from the end of the deploying catheter. A tight spacing between layers may result in interference between the various layers during deployment and a random (rather than regular) shape after completion of the deployment.

The material used in vaso-occlusive member (100) may be any of a wide variety of materials; preferably, the wire is a radio-opaque material such as a metal or a polymer. Suitable metals and alloys for the wire making up the primary coil (102) include the Platinum Group metals, especially platinum, rhodium, palladium, rhenium, as well as tungsten, gold, silver, tantalum, and alloys of these metals. These metals have significant radiopacity and in their alloys may be tailored to accomplish an appropriate blend of flexibility and stiffness. They are also largely biologically inert. Highly preferred is a platinum/tungsten alloy.

The wire may also be of any of a wide variety of stainless steels if some sacrifice of radiopacity may be tolerated. Very desirable materials of construction, from a mechanical point of view, are materials which maintain their shape despite being subjected to high stress. Certain "super-elastic alloys" include nickel/titanium alloys (48–58 atomic % nickel and optionally containing modest amounts of iron); copper/zinc alloys (38–42 weight % zinc); copper/zinc alloys containing 1–10 weight % of beryllium, silicon, tin, aluminum, or gallium; or nickel/aluminum alloys (36–38 atomic % aluminum). Particularly preferred are the alloys described in U.S. Pat. Nos. 3,174,851; 3,351,463; and 3,753,700. Especially preferred is the titanium/nickel alloy known as "nitinol". These are very sturdy alloys which will tolerate significant flexing without deformation even when used as a very small diameter wire.

If a superelastic alloy such as nitinol is used in the device, the diameter of the coil wire may be significantly smaller than that used when the relatively more ductile platinum or platinum/tungsten alloy is used as the material of construction.

Finally, the overall diameter of the device (100) is generally between 3 and 12 millimeters. Most aneurysms within the cranial vasculature can be treated by one or more devices having those diameters. Of course, such diameters ar not a critical aspect of the invention.

The coils may be made of radiolucent fibers or polymers (or metallic threads coated with radiolucent or radiopaque fibers) such as Dacron (polyester), polyglycolic acid, polylactic acid, fluoropolymers (polytetrafluoro-ethylene), Nylon (polyamide), or even silk. Should a polymer be used as the major component of the vaso-occlusive member (100), it is desirably filled with some amount of a known radiopaque material such as powdered tantalum, powdered tungsten, bismuth oxide, barium sulfate, and the like.

Generally speaking, when the device (100) is formed of a metallic coil as the vaso-occlusive member (102) and that coil is a platinum alloy or a superelastic alloy such as nitinol, the diameter of the wire used in the production of the coil will be in the range of 0.0005 and 0.006 inches. The wire of such diameter is typically then wound into a primary coil (102) having a primary diameter of between 0.005 and 0.025 inches. For most neurovascular indications, the preferable diameter is 0.010 to 0.018 inches. We have generally found that the wire may be of sufficient diameter to provide a hoop strength to the resulting device sufficient to hold the device in place within the chosen body cavity without distending the wall of the cavity and without moving from the cavity as a result of the repetitive fluid pulsing found in the vascular system.

The axial length of the primary shape will usually fall in the range of 0.5 to 100 cm, more usually 2 to 40 cm. Depending upon usage, the coil may well have 10–75 turns per centimeter, preferably 10–40 turns per centimeter. All of the dimensions here are provided only as guidelines and are not critical to the invention. However, only dimensions suitable for use in occluding sites within the human body are included in the scope of this invention.

A variation of this invention includes helically wound primary coils (102) having at least one region having a greater flexibility than some other section of the coil. This allows tailoring of the resulting device (100) for particular purposed. For instance, for use in thin-walled aneurysms, a device (100) having an outer layer (110) and perhaps a second layer (106) of a softer material might be desirable. This softening of some portion of the device may be accomplished in a variety of ways, e.g., by altering the pitch spacing or angle of the primary winding or by changing the diameter of the wire or the primary coil in certain regions. The coil section may be annealed to soften the metal in the coil section.

Other uses may require stiffer outer sections in the device (100).

Also contemplated in this invention is the attachment of various fibrous materials to the inventive coil (100) for the purpose of adding thrombogenicity to the resulting assembly. The fibrous materials may be attached in a variety of ways. A series of looping fibers may be looped through or tied to coil and continue axially down the coil. Another variation is by tying the tuft to the coil. Tufts may be tied at multiple sites through the coil to provide a vast area of embolus forming sites. The primary coil may be covered by a fibrous braid. The method for producing the former variation is described in U.S. Pat. Nos. 5,226,911 and 5,304,194 to Chee. The method of producing the fibrous braid is described in U.S. Pat. No. 5,382,259, issued Jan. 17, 1995, to Phelps and Van.

Figure 2A:
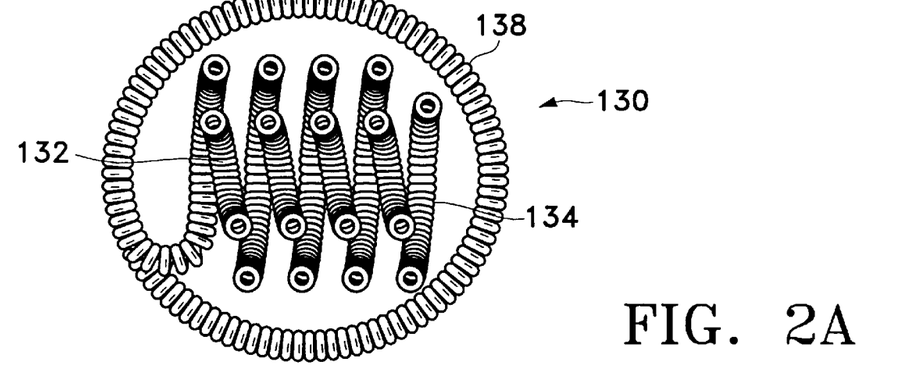
FIG. 2A shows a cross sectional side view of a vaso-occlusive coil made according to the invention having two axes of winding.
Figure 2B:
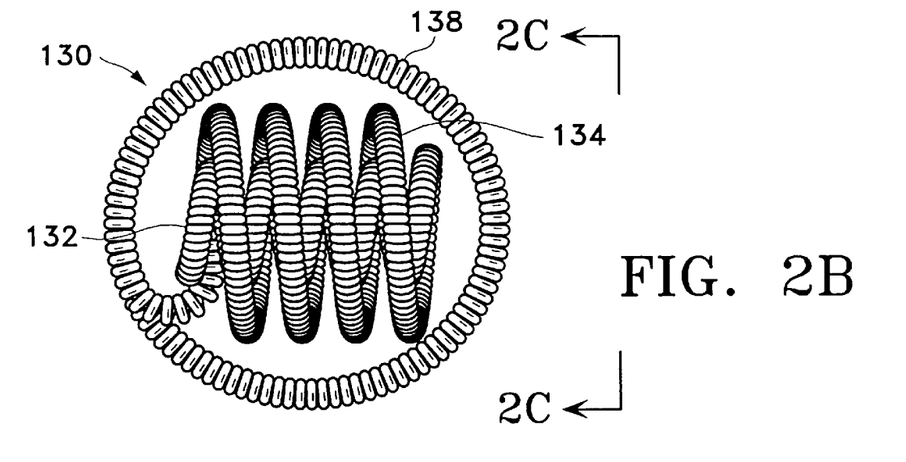
FIG. 2B shows a side view of the vaso-occlusive coil of FIG. 2A.
Figure 2C:
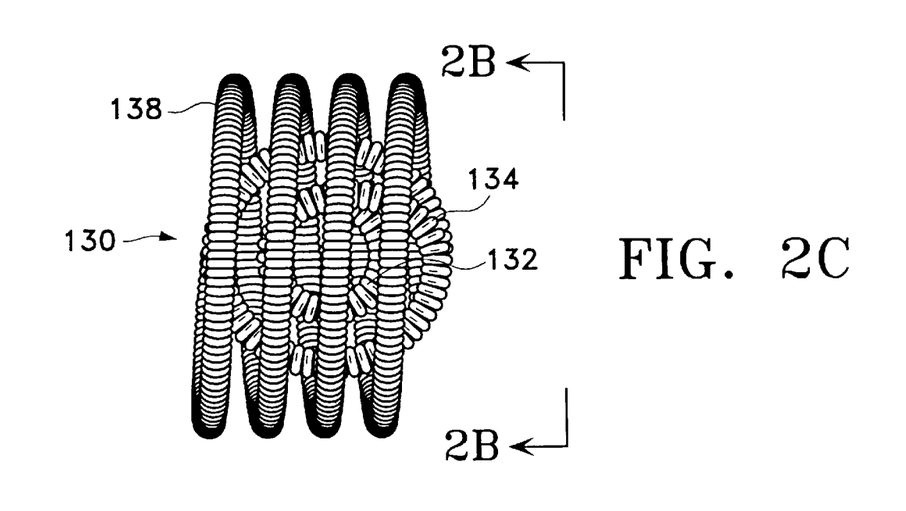
FIG. 2C shows a partial cross-sectional end view of the vaso-occlusive coil of FIG. 2A.

FIGS. 2A, 2B, and 2C show a variation of the invention in which the vaso-occlusive device (130) is wound in such a way that the various layers of the device are not centered about a single axis.

FIG. 2A shows a side-view cross-section of a second variation of this invention, a coil (130). This variation is also made up of a primary coil which was initially wound in a linear form and that linear coil (shown as (102) in FIG. 1A) is then wound into the secondary form shown. This coil (130) also has three layers of secondary windings. The inner winding (132) is first wound and the second layer (134) is found on top of the first layer (132). The second layer (134) in this instance has approximately the same longitudinal axis (132) as the first layer (132).

In the FIG. 2B variation, the vaso-occlusive coil (130) has an outer layer (138) which is wound having on an axis different than the axis of the two inner coil layers (132 and 134). Different than the FIGS. 1A–1C variation, the outer layer (130) has a fairly long axial length. This configuration is also a stepped shape approximating a sphere, ovoid, or egg. This variation has a propensity to self-form with a bit greater ease than the variation discussed above since the outer layer does not have so far to travel within the vascular wall as does the primary coil in the FIGS. 1A–1C variation. Other shapes may also be easily formulated using the concepts described herein.

FIG. 2C shows a partial cutaway, end view of the inventive device (130). FIG. 2C shows the inner layer (132), second layer (134), and outer layer (138).

Figure 3:
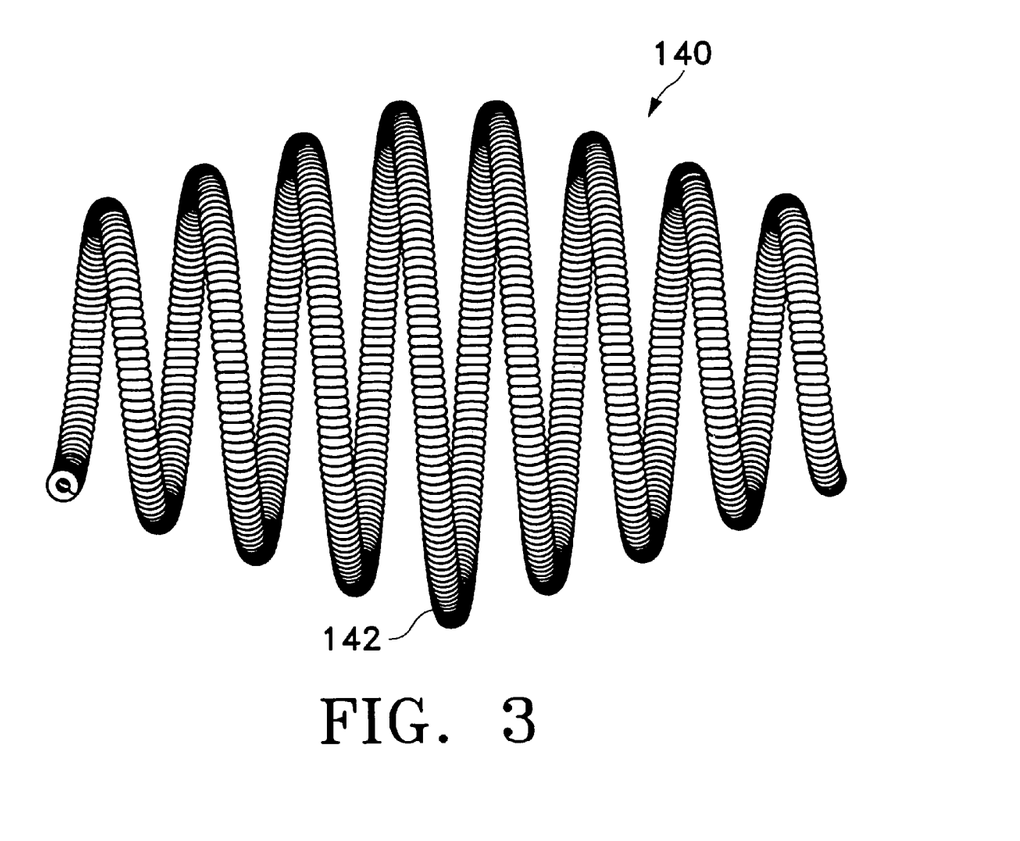
FIG. 3 is a side view of a coil made according to the invention in which the outer profile is not cylindrical.

FIG. 3 shows a side view of a vaso-occlusive device (140) made according to this invention having a secondary shape which is not columnar. In this instance the exemplified overall secondary shape is ovoid. This variation is merely an example of the outer shapes which may be selected to perform specified occlusive tasks. The inner layers (not shown in FIG. 3) may either correspond in shape to the outer layer (142) or may be columnar or tubular as is shown in the earlier Figures. Specific secondary shapes are not critical to this invention.

Figure 4:
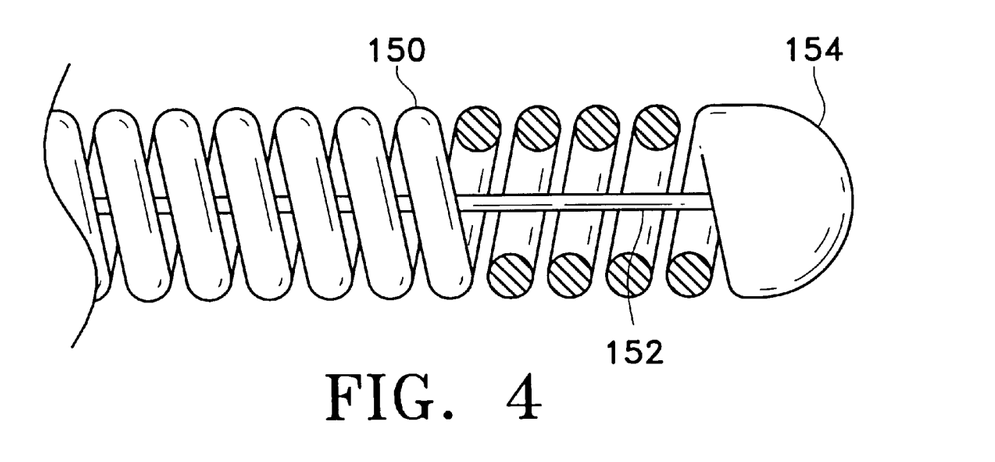
FIG. 4 shows a magnified partial side view of a device for the purpose of showing the interior stretch resisting strand.
Figure 5A:
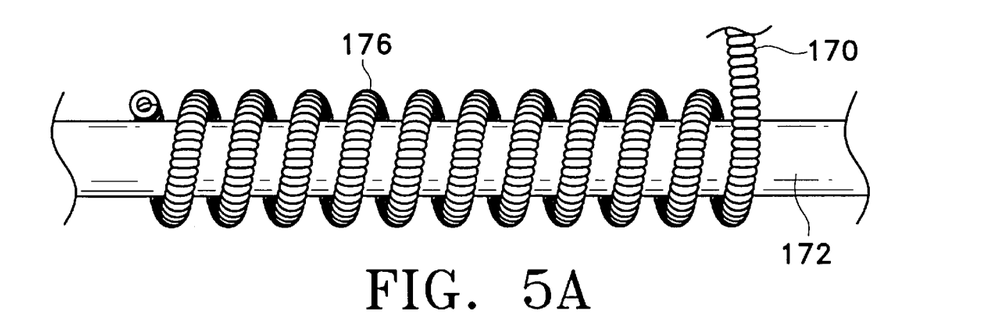
FIG. 5 shows a procedure for winding a coil such as shown in FIGS. 1A to 1C according to the invention.
Figure 5B:
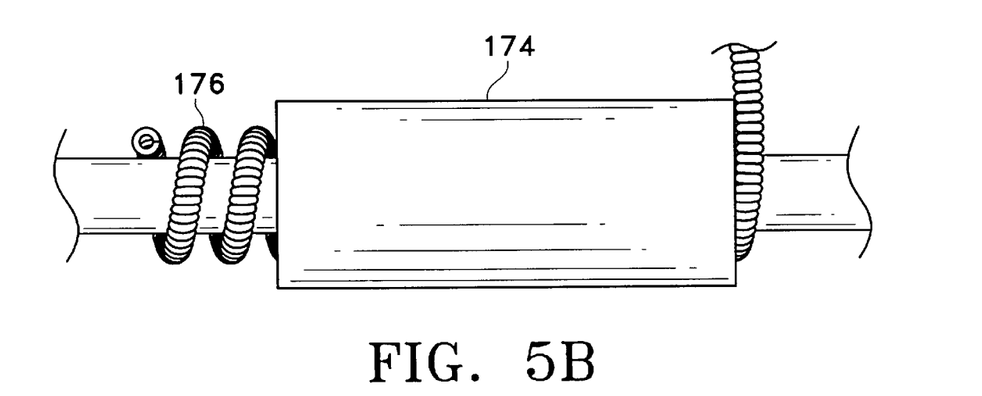
Figure 5C:
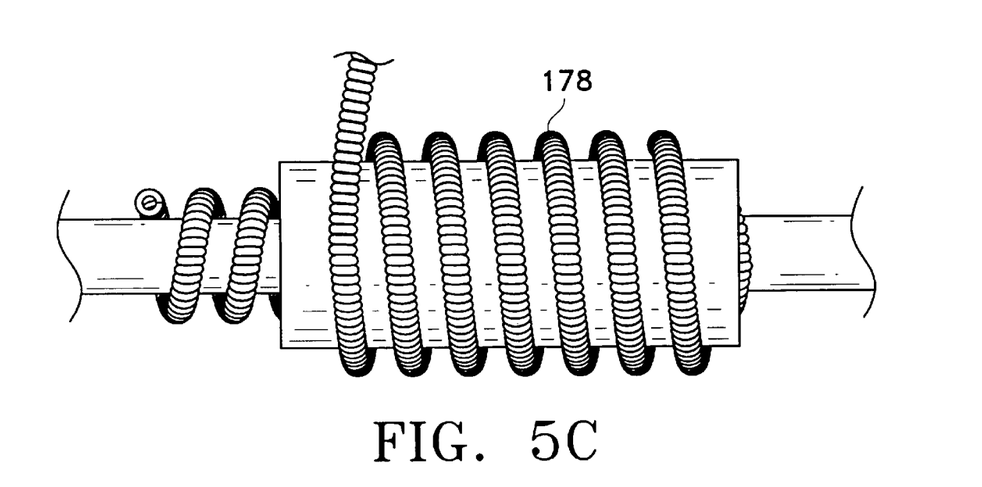
Figure 5D:
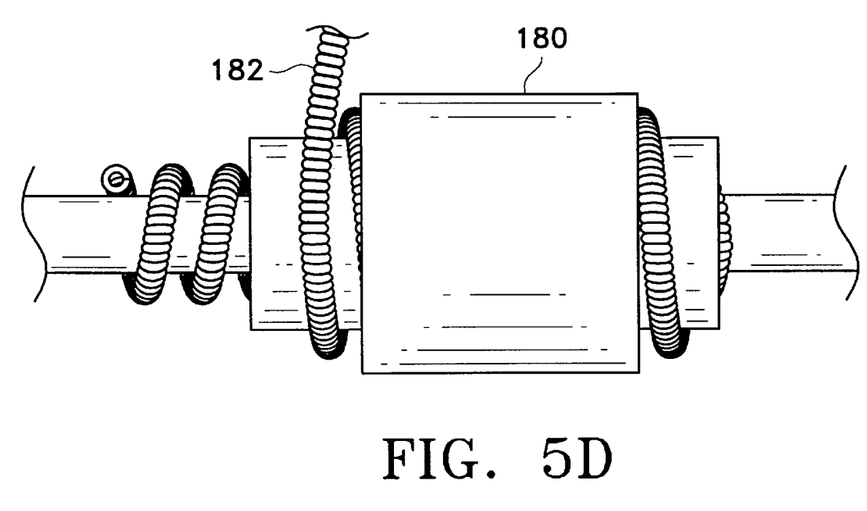
Figure 5E:
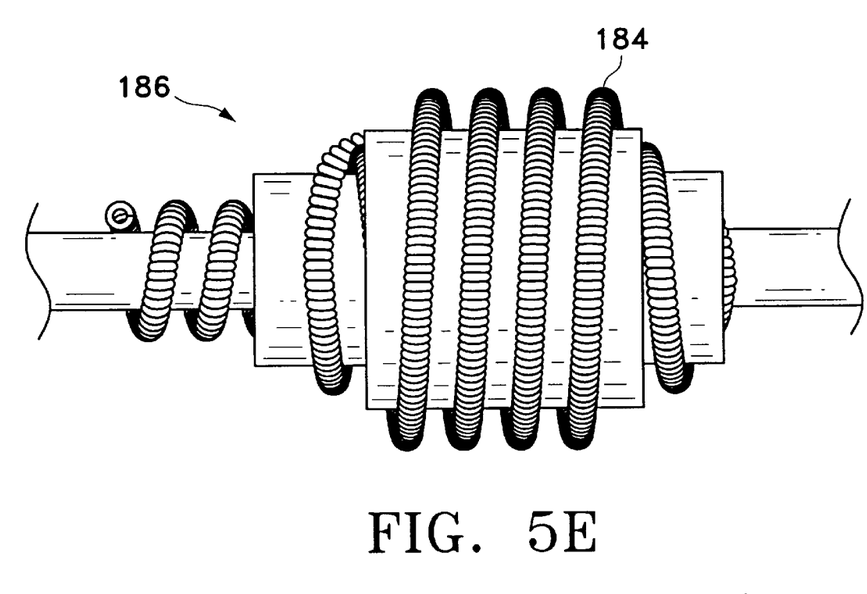
Figure 6A:
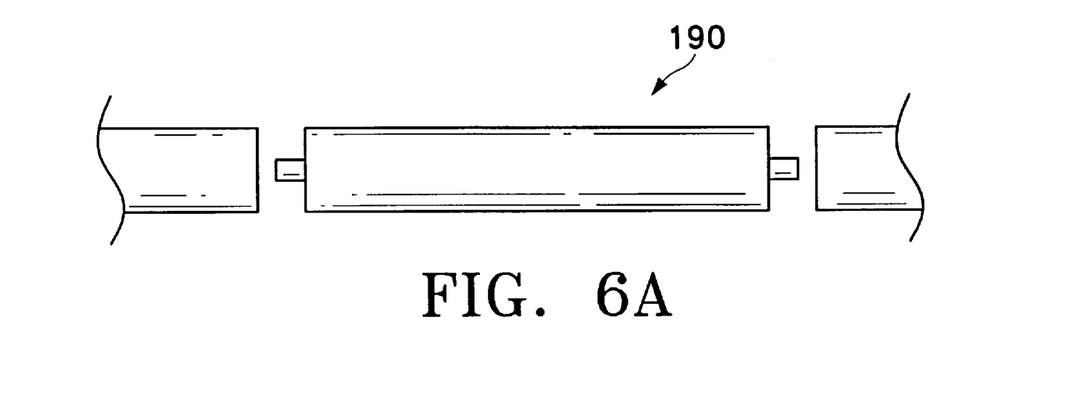
FIG. 6 shows a procedure for winding a coil such as shown in FIGS. 2A to 2C according to the invention.
Figure 6B:
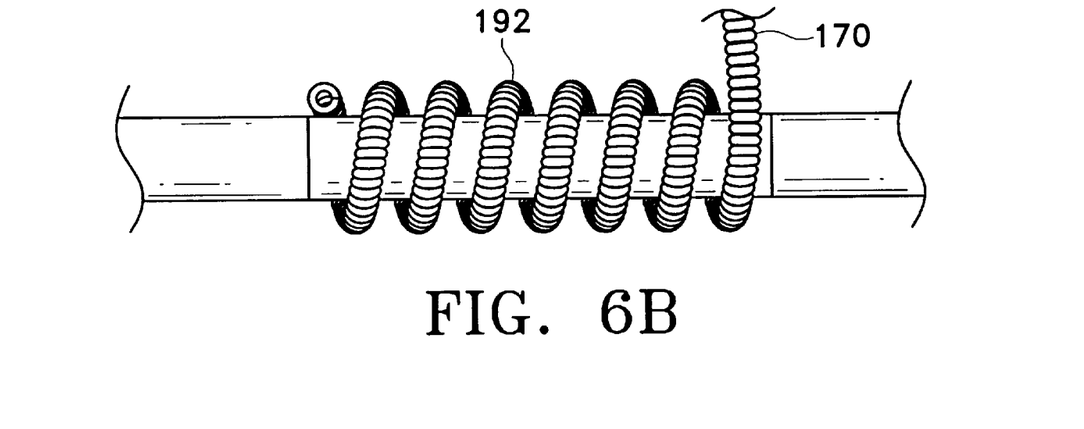
Figure 6C:
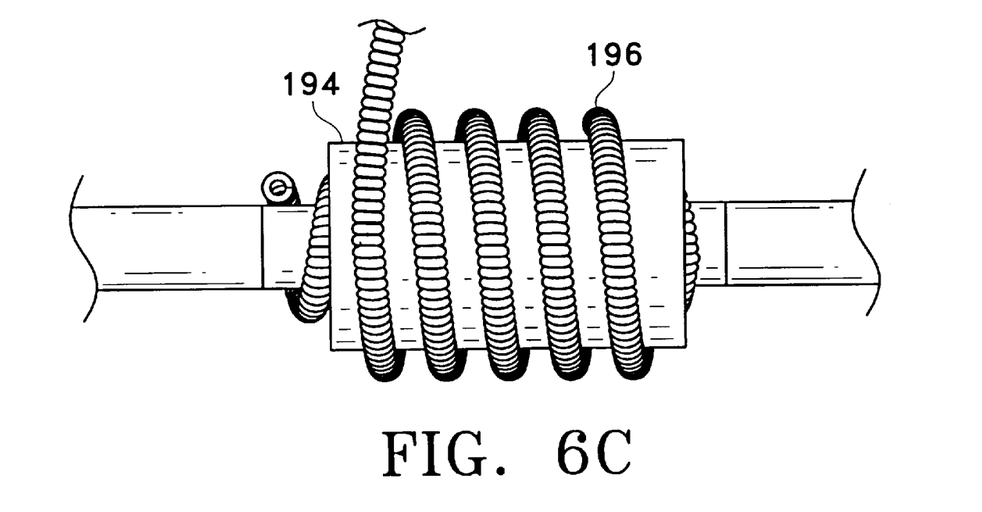
Figure 6D:
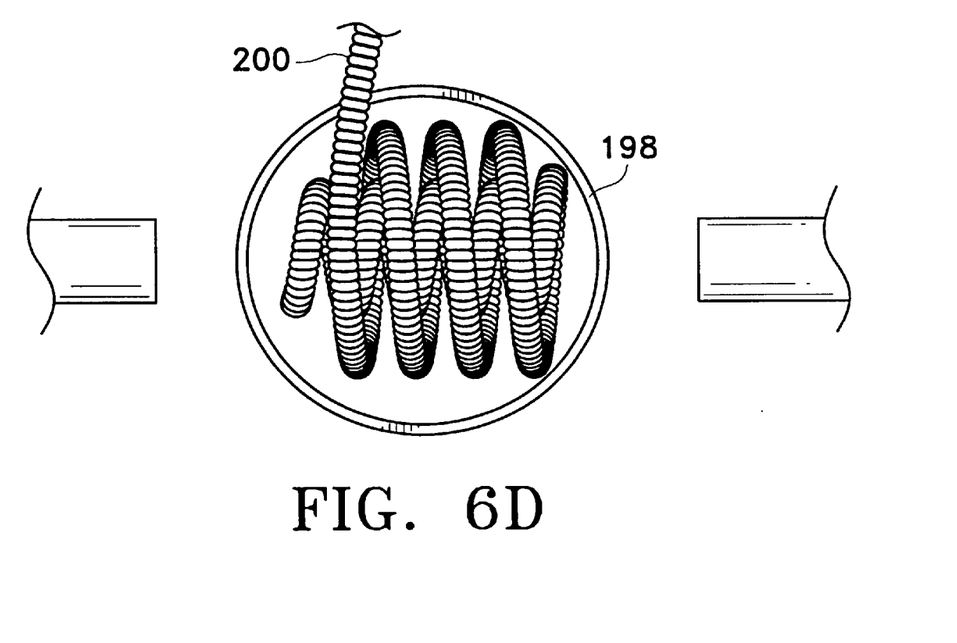
Figure 6E:
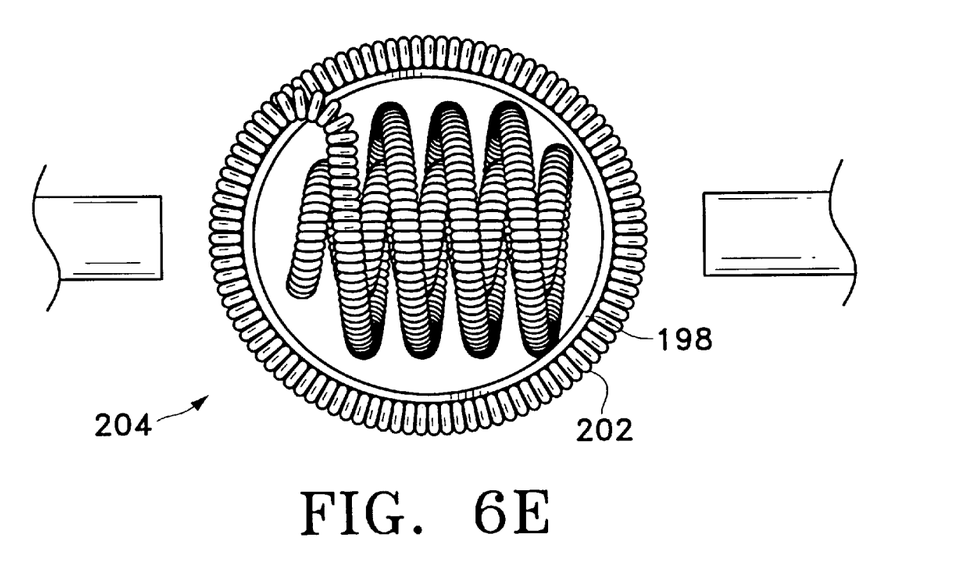

FIG. 4 shows a desirable variation of the invention in which the primary winding (150) is reinforced with an inner wire (152) which runs from end to end of the primary winding (150). The reinforcing wire (152) is for the purpose of preventing the occurrence of stretching during those instances in which the coil is moved from site to site within the human body. In this variation, the reinforcing wire (152) is a small wire of the same composition as is the coil wire material and is melted into the tip (154) of the primary winding (150) to form a sturdy joint.

Although methods for production of the inventive devices may be apparent to the skilled worker based upon our description of the device, FIGS. 5 and 6 show a desirable method for producing the devices shown, respectively, in FIGS. 1A–1C and in FIGS. 2A–2C.

FIG. 5 shows a method for winding the FIGS. 1A–1C device. Prior to step 1 in the Figure, a portion of wire is first wound to produce a linear coil (170). In step 1, the linear coil is then wound onto a mandrel (172) to match the pitch criteria discussed above. It is common to anneal the linear coil to prevent it from unwinding during these later fabrication steps. Step 2 shows the installation of a tubular mandrel (174) onto the outside of inner layer (176). In step 3, another length of the primary linear coil is wound from right to left in drawing to produce a second layer (178). An additional tubular mandrel (180) is then added to the outer surface of second layer (178). The remaining length (182) of primary linear coil is then wound from left to right in the drawing to produce the outer layer (182). The complete assemblage (186) of coil and mandrels is then subjected to an appropriate annealing step to set the secondary shape (see, FIG. 1B) prior to disassembly of the fabrication apparatus and loading of the coil into a carrier for introduction into the delivery catheter. The various mandrels shown are of sufficient heat resistance to allow such annealing steps. The mandrels are typically made of a refractory material such as alumina or zirconia (for heat-treating devices made of purely metallic components) or may be made of a ball of a metallic coil material. The function of the mandrels is simply to form a support for winding, not pollute the device during the heat-treatment step, and provide a specific form to the device during that heat-treatment step. A typical annealing step for a platinum/tungsten alloy would involve a 1100° F. heating step in air for about 15–20 minutes.

Should the make-up of the vaso-occlusive element not be solely metal—in that it contains readily meltable plastic or the like—the temperature at which the heat treatment takes place is significantly lower and typically for a significantly shorter period of time. The flexural modulus of most plastics being significantly lower than those of metals, the bulk of the polymer-based device will be significantly larger than that of the metal-based device.

FIG. 6 shows a similar procedure. Step 1 shows the assembly of a three-part mandrel (190). The assembled mandrel is then wound in Step 2 with a primary linear coil (170) to form an inner winding (192). a tubular mandrel (194) is then wound with the linear coil to produce a second layer (196) much in the manner described in steps 2 and 3 of FIG. 6. In step 4, the inner mandrel assembly (196) is disassembled and a generally tubular mandrel (198) is placed about the thusly wound coil. The outer mandrel (198) has an axis which is generally orthogonal to the axis of the inner mandrel (190) but obviously need not be so. The stub (200) of the linear coil is then wound about the outer mandrel (198) to produce outer layer (202). The assembly (204) may then be annealed in the manner discussed above. The assembly may then be taken apart, the coil extended and introduced into a carrier for later delivery via a catheter.

Figures 7A, 7B, 7C, 7D:
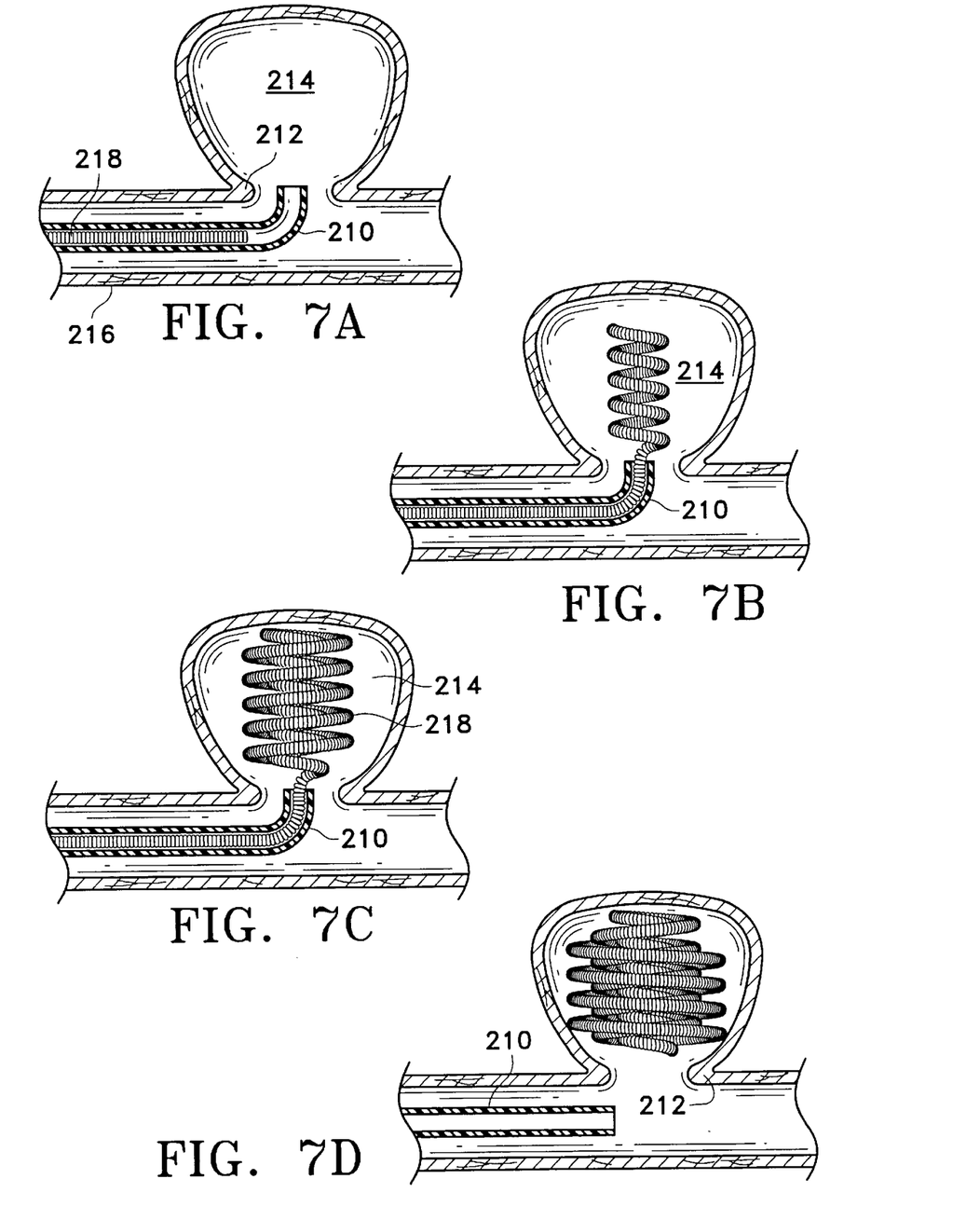
FIG. 7 shows a procedure for introducing a vaso-occlusive coil such as in FIGS. 1A to 1C into an aneurysm.

FIG. 7 depicts a common deployment method for introduction of the inventive vaso-occlusive devices described here. It may be observed that these procedures are not significantly different than those described in the Ritchart et al. patent mentioned above. The major difference in the procedure is the ability of the vaso-occlusive device to form the secondary shapes discussed above as the coil exits the catheter. Specifically, Step 1 shows the distal tip of a delivery catheter (210) which is within the opening (212) of an aneurysm (214) found in an artery (216). The distal or end section of the vaso-occlusive device (218) is shown within the catheter (210). In Step 2, the distal end portion of the vaso-occlusive device (218) has exited the distal end of the catheter (210) and has "self-wound" to form the inner layer of the vaso-occlusive device (218) within the aneurysm (214). Step 3 shows the winding of the second layer of the vaso-occlusive device (218). Step 4 shows the final wrapping of the outer layer of the vaso-occlusive device (218) within the aneurysm (214) and the withdrawal of the catheter from the mouth of the catheter (210).

Figure 8:
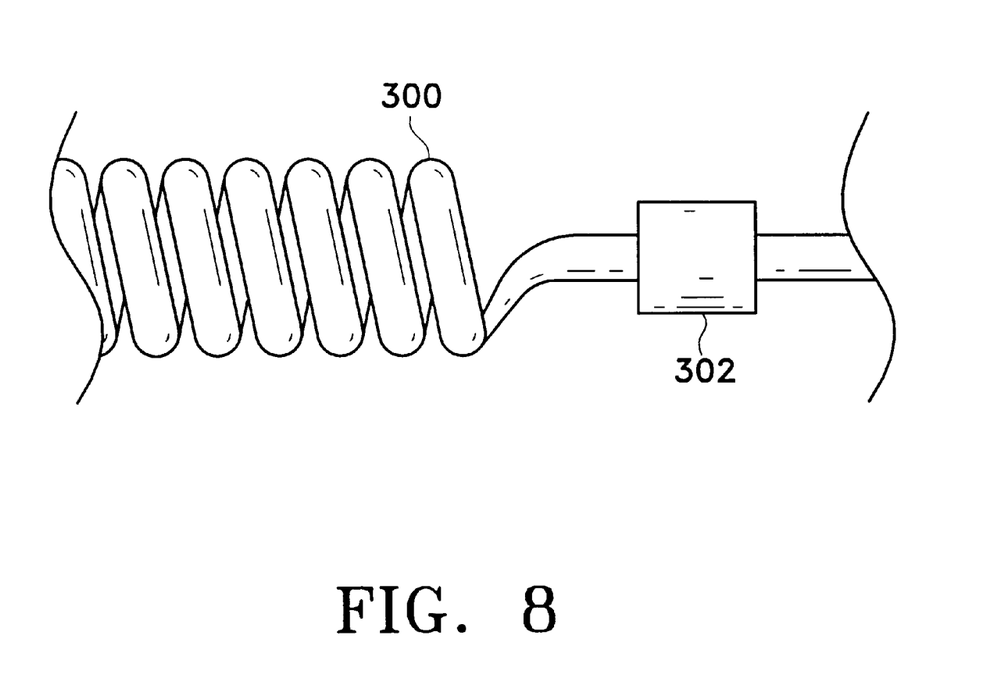
FIG. 8 shows a coil of the subject invention having a deployment tip.

FIG. 8 depicts the vaso-occlusive devices described herein (300) having a deployment tip (302) such as the mechanical and electrolytic detachable joints described above.

Modification of the above-described variations of carrying out the invention that would be apparent to those of skill in the fields of medical device design generally, and vaso-occlusive devices specifically, are intended to be within the scope of the following claims.

We claim as our invention:

1. A vaso-occlusive device comprising a primary coil having a proximal end and a distal end constructed of a plurality of helically wound turns of a biocompatible wire and having a secondary form having a single longitudinal axis with at least a first section having a first section end and a second section, said first and second sections constructed of a plurality of helically wound turns of said primary coil, wherein said second section is at least partially surrounded by said first section and wherein the overall secondary form of the vaso-occlusive device is self-forming in the approximate shape of a sphere or ovoid.

2. The device of claim 1 further comprising a reinforcement which runs from the distal end to the proximal end of the primary coil.

3. The device of claim 2 wherein the reinforcement is wire.

4. The device of claim 1 comprising a metal selected from the group consisting of platinum, palladium, rhodium, gold, tungsten, and their alloys.

5. The device of claim 4 comprising an alloy of platinum and tungsten.

6. The device of claim 1 comprising an alloy selected from the group consisting of stainless steels and superelastic alloys.

7. The device of claim 6 wherein the alloy is nitinol.

8. The device of claim 1 comprising a polymer containing a radio-opaque filler.

9. The device of claim 1 additionally comprising attached polymeric fibers.

10. The device of claim 1 wherein the primary coil has regions which are relatively more flexible than other regions of the primary coil.

11. The device of claim 1 additionally a deployment tip attached to at least one of proximal or distal ends of the primary coil.

12. The device of claim 11 wherein the deployment tip comprises a mechanically detachable end adapted to attach to and detach from a pusher.

13. The device of claim 11 wherein the deployment tip comprises an electrolytically detachable end adapted to detach from a pusher by imposition of a current on said pusher.

14. A vaso-occlusive device comprising a primary coil constructed of a plurality of helically wound turns of a biocompatible wire and having a secondary form with at least a first section and a second section, said first and second sections constructed of a plurality of helically wound turns of said primary coil, said first section having a longitudinal axis, said second section having a longitudinal axis different than said first section, wherein said second section is at least partially surrounded by said first section and wherein the overall secondary form of the vaso-occlusive device is self-forming in the approximate shape of a sphere or ovoid.

15. The device of claim 14 further comprising a reinforcement which runs from the distal end to the proximal end of the primary coil.

16. The device of claim 15 wherein the reinforcement is wire.

17. The device of claim 14 comprising a metal selected from the group consisting of platinum, palladium, rhodium, gold, tungsten, and their alloys.

18. The device of claim 17 comprising an alloy of platinum and tungsten.

19. The device of claim 14 comprising an alloy selected from the group consisting of stainless steels and superelastic alloys.

20. The device of claim 19 wherein the alloy is nitinol.

21. The device of claim 14 comprising a polymer containing a radio-opaque filler.

22. The device of claim 14 additionally comprising attached polymeric fibers.

23. The device of claim 14 wherein the primary coil has regions which are relatively more flexible than other regions of the primary coil.

24. The device of claim 14 wherein the primary coil additionally comprises a deployment tip attached to the proximal end.

25. The device of claim 24 wherein the deployment tip comprises a mechanically detachable end adapted to attach to and detach from a pusher.

26. The device of claim 24 wherein the deployment tip comprises an electrolytically detachable end adapted to detach from a pusher by imposition of a current on said pusher.

* * * * *